United States Patent [19]

Yamamoto et al.

[11] Patent Number: 4,558,425
[45] Date of Patent: Dec. 10, 1985

[54] NMR IMAGING APPARATUS OF CHANGEABLE INSPECTING ZONE SIZE

[75] Inventors: Etsuji Yamamoto; Kensuke Sekihara, both of Hachioji; Hideki Kohno, Suginami; Shinji Yamamoto, Hachioji, all of Japan

[73] Assignee: Hitachi, Ltd., Tokyo, Japan

[21] Appl. No.: 413,821

[22] Filed: Sep. 1, 1982

[30] Foreign Application Priority Data

Sep. 4, 1981 [JP] Japan .................................. 56-138572

[51] Int. Cl.[4] .......................................... G01N 15/00
[52] U.S. Cl. ................................... 364/555; 324/313; 364/414; 378/4
[58] Field of Search .............. 364/413, 414, 415, 527, 364/555; 324/309, 313; 378/4, 16; 367/900, 903; 356/5

[56] References Cited

U.S. PATENT DOCUMENTS

| 4,110,681 | 8/1978 | Hofer et al. | 324/313 |
| 4,184,110 | 1/1980 | Hinshaw | 324/313 X |
| 4,208,731 | 6/1980 | Desbrandes | 367/900 X |
| 4,221,004 | 9/1980 | Combs et al. | 367/900 X |
| 4,344,705 | 8/1982 | Kompa et al. | 356/5 |

OTHER PUBLICATIONS

Pykett, Ian L.; "NMR Imaging in Medicine"; Scientific American.

Primary Examiner—Errol A. Krass
Assistant Examiner—Kevin J. Teska
Attorney, Agent, or Firm—Antonelli, Terry & Wands

[57] ABSTRACT

In an imaging apparatus using nuclear magnetic resonance which includes apparatus for generating a static magnetic field, a linear gradient magnetic field and a radio frequency magnetic field, respectively, signal detection device for detecting the nuclear magnetic resonant signal from an object to be inspected, a computer for calculating from the detection signal an image and output device for displaying the result of calculation by the computer, the improvement wherein the size of the object to be inspected is detected by use of ultrasonic wave or light beams and a signal indicative of the detected size of the object is applied to the linear gradient magnetic field generation apparatus so as to control the intensity of the linear gradient magnetic field.

17 Claims, 5 Drawing Figures

NMR IMAGING APPARATUS OF CHANGEABLE INSPECTING ZONE SIZE

BACKGROUND OF THE INVENTION

This invention relates to an imaging apparatus for non-destructively determining the density distribution, relaxation time distribution or the like, of nuclear spin inside an object to be inspected by use of nuclear magnetic resonance (NMR). More particularly, the present invention relates to an imaging apparatus using nuclear magnetic resonance which apparatus has especially improved spatial resolution.

X-ray CT (computed tomography) and ultrasonic imaging apparatuses have gained conventionally a wide application as apparatuses for non-destructively inspecting the internal structure of a human body or the like. Recently, attempts to carry out the similar inspection by use of nuclear magnetic resonance have proved successful and it has been clarified that this NMR technique provides the data that can not be obtained by the X-ray CT and the ultrasonic imaging apparatuses.

Imaging apparatuses using nuclear magnetic resonance determine non-destructively data relating nuclear magnetic resonance such as the density distribution and relaxation time distribution of the nuclear spin inside the object to be inspected from outside the object, and reconstructs and produces the cross section of a desired measuring target of the object in the same way as in the X-ray CT.

Various methods have been proposed in the past to detect various NMR data such as the density distribution and relaxation time distribution of the nuclear spin in the imaging apparatuses using nuclear magnetic resonance. With the exception of a magnetic focusing method, most of these methods place the nuclear spin to be discriminated in a specific static magnetic field by use of linear gradient magnetic fields that are perpendicular to each other, and put the coordinates to the nuclear spin. In this case, the resonant frequency of the nuclear spin is determined by the sum of the intensity of the linear gradient magnetic fields and the static magnetic field and hence, the spin position can be detected by analyzing the nuclear signal.

In the imaging apparatuses that have been proposed to date, it has not been attempted to apply the linear gradient magnetic field having the intensity corresponding to the size of the object to be inspected or the size of an inspection zone.

For this reason, if the object to be inspected is a human body, for example, the spatial resolution in the case of inspection of the head becomes the same as the spatial inspection of the bust. If the object to be inspected is small such as the head, the number of elements for reconstructing the image representative of the head becomes small and the image becomes more rough in comparison with the bust.

SUMMARY OF THE INVENTION

The present invention is therefore directed to provide an imaging apparatus using nuclear magnetic resonance which can obtain optimal spatial resolution in accordance with the size of the object to be inspected or the size of the inspection zone.

In an imaging apparatus using nuclear magnetic resonance, the object of the present invention can be accomplished by changing the intensity of the linear gradient magnetic field in accordance with the size of the object to be inspected or the size of the inspection zone.

If the intensity of the linear gradient magnetic field remains constant irrespective of the object to be inspected, the band of the resonant signal is proportional to the size of the object to be inspected or to the size of the inspection zone. Accordingly, if the object is small, the sampling number of the object decreases unless the sampling frequency is changed. However, since the upper limit of the sampling frequency is determined with respect to the object of the greatest size, the increase of the sampling frequency for a small object to be inspected becomes meaningless. For this reason, the present invention improves the spatial resolution by increasing the intensity of the linear gradient magnetic field for a small inspection object and enlarging the signal band so as to increase the sampling number.

DESCRIPTION OF THE PREFERRED EMBODIMENTS

Figure 1:
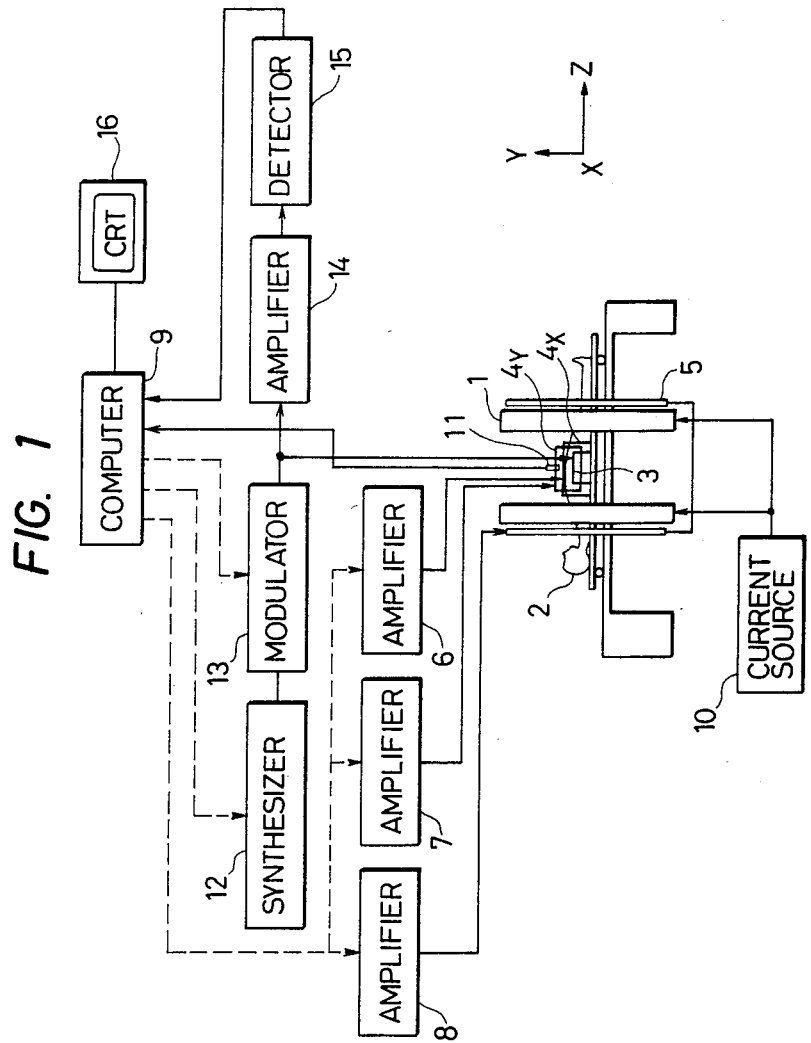
FIG. 1 shows the construction of the imaging apparatus in accordance with one embodiment of the present invention.

FIG. 1 shows the construction of the imaging apparatus in accordance with one embodiment of the present invention. In the drawing, reference numeral 1 represents a coil for generating a static magnetic field in the Z direction and reference numeral 2 represents an object to be inspected (a human body, in this case). Reference numeral 3 represents a coil for generating a radio frequency magnetic field and reference numerals $4_X$ and $4_Y$ represent coils for generating the linear gradient fields in X and Y directions, respectively. (Refer to the arrows on the lower right of FIG. 1 for the directions, with the proviso that the X direction faces upward in the direction prerpendicular to the drawing.)

Figure 2:
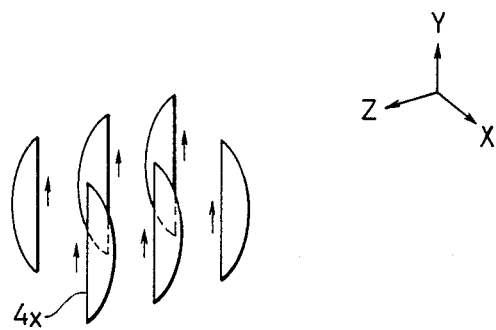
FIG. 2 shows an example of the coil for generating the linear gradient magnetic field.

FIG. 2 shows the construction of the coil $4_X$ for generating the linear gradient magnetic field in the X direction. The arrows in the drawing represent the directions of current. The coil $4_Y$ for generating the linear gradient magnetic field in the Y direction corresponds to one that is obtained by rotating the coil $4_X$ shown in FIG. 2 by 90° around the Z axis. Reference numeral 5 represents a coil for generating the linear gradient magnetic field in the Z direction and one-turn coils wired in such a manner that currents flow in the opposite directions are employed.

Reference numerals 6, 7 and 8 represent amplifiers for feeding a current to each of the coils $4_X$, $4_Y$ and 5, respectively, and reference numeral 10 represents a constant current source for feeding a constant current to the coil 1.

The coil 3 for generating the radio frequency magnetic field has the function of generating the radio frequency magnetic field and also the function of detecting a nuclear magnetic resonant signal generated from the object 2 to be inspected. A saddle-shaped, solenoidal or one-turn type coil is used as the coil 3.

The amplifiers 6, 7 and 8 are controlled by signals from a computer 9 and the time of application and waveshape are determined. The intensity of the linear gradient magnetic fields generated by the coils $4_x$, $4_y$ and 5 can be changed by a detector 11 for detecting the size of the object 2 to be inspected or by the instruction from the operator of the imaging apparatus of the present invention.

Next, the signal transmission system will be described. The radio frequency generated by a frequency synthesizer 12 is subjected to wave shaping and power amplification by a modulator 13 and a current is applied to the coil 3, thereby generating the radio frequency magnetic field for exciting the nuclear spin. Both synthesizer 12 and modulator 15 are controlled by the computer 9 and the frequency of the radio frequency, the time of application, the pulse width and the like are determined. The object 2 to be inspected is inserted into the coil 1 for radio frequency magnetic field and the linear gradient magnetic fields are applied to the generated static magnetic field $H_o$. The signal from the object 2 to be inspected is received by the coil 3, passes through the amplifier 14, is then subjected to the quadrature detection by a detector 15 and is thereafter applied to the computer 9. After processing the signal, the computer 9 displays an image corresponding to the nuclear spin distribution or to the nuclear spin relaxation time distribution on a CRT display 16.

In the imaging apparatus of this embodiment, the detector 11 detects the size of the object 2 to be inspected in the non-contact arrangement and the intensity of the linear gradient magnetic fields is changed in accordance with the size of the object 2 to be inspected so as to obtain an image having the best spatial resolution corresponding to the object to be inspected.

Next, the reason why the intensity of the linear gradient magnetic field is variable in accordance with objects to be inspected will be explained in detail. In nuclear magnetic resonance, the resonant frequency $f_o$ is proportinal to the static magnetic field $H_o$ in which nuclear spin is placed, and is expressed by the following formula:

$$f_o = \frac{\gamma}{2\pi} H_o \quad (1)$$

Figure 3:
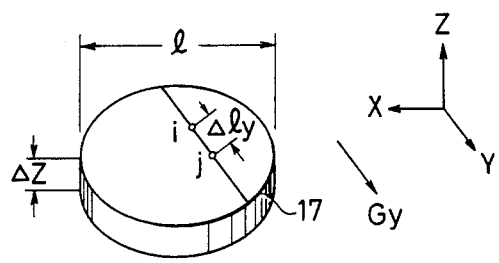
FIG. 3 shows the principle of the present invention.

Here, $\gamma$ is referred to as a "magnetogyric ratio" and has a value $2.675 \times 10^4$ Hz·Gauss$^{-1}$ in the case of proton. It will now be assumed that an object 17 having a diameter l and a thickness $\Delta Z$ is inspected, as shown in FIG. 3. Various methods have been proposed in the past to measure the nuclear spin distribution or relaxation time distribution in this object, but the present invention will be explained with reference to a projection-reconstructon method proposed by Lauterbur (Nature, 242, 190 (1973)), by way of example. This method makes use of the fact that when the linear gradient magnetic fields are applied to a given object from various directions and the resulting signals are viewed on the axis of frequency, an integrated signal can be obtained inside a plane perpendicular to the inclination. In nuclear magnetic resonance, the nuclear spins inside the same static magnetic field cause resonance at the same frequency, as can be understood from the formula (1) and the nuclear spins inside the plane perpendicular to the inclination have the same resonant frequency. The distribution of the original spins can be obtained from the projection data thus obtained, in exactly the same way as in X-ray CT.

Now, the resonant signal from the object to be inspected, that is shown in FIG. 3, has a line width characterized by the transversal relaxation time $T_2$· even under the state in which no linear gradient magnetic field is applied, and its shape function is generally Lorentian and is expressed by the following formula:

$$P(\omega) = \frac{T_2^*}{\pi} \cdot \frac{1}{1 + T_2^{*2}(\omega - \omega_0)^2} \quad (2)$$

where $\Phi_o$ is a central angular frequency and $\omega$ is an angular frequency at the time of observation.

It will be now assumed that a linear gradient magnetic field $G_y$ is applied in the Y direction and an integrated signal of the nuclear spins from the line extending in the Y direction is detected. To discriminate signals from two points i and j that are spaced apart from each other by a distance $\Delta l_y$, the linear gradient magnetic field $G_y$ must satisfy the following relation:

$$G_y \geq \frac{2}{\gamma T_2^*} \cdot \frac{1}{\Delta l_y} \quad (3)$$

In other words, it is the condition that the center frequency of the resonance signals from the two points i and j is separated by at least a resonant line width and both can be separated from each other. Since this condition holds true of the signals from all the spins on the line in the X direction, the formula (3) is a relational formula providing the lower limit of the intensity of the linear gradient magnetic fields necessary for projection-reconstruction. The separation can of course be improved if $G_y$ is increased, but with a greater resonant line width and with decreasing amplitude, inviting eventually the drop of an S/N ratio. Hence, $G_y$ can not be increased unlimitedly.

To obtain the image of the original nuclear spins from the projection data such as described above, it is necessary to sample the signals in the same way as in X-ray CT and to perform calculation for the image reconstruction. The upper limit of the sampling frequency is determined by the resonant line width and resoltution can be hardly improved even if the sampling frequency is increased above twice the line width. Hence, this frequency is referred to as a "limit of sampling frequency".

It will be therefore assumed that $2/(rT_2^* \cdot \Delta l_y)$ is applied as the linear gradient magnetic field $G_y$ to the bust of a diameter $l_B$ as the object and the limit of sampling frequency $$\left(= \frac{1}{\pi r T_2^*}\right)$$

is selected as the sampling frequency. In this case, the data number $l_B/l_y$ can be obtained. Next, it will be assumed that inspection of the head having a diameter $l_h (l_h < l_B)$ is conducted using the same apparatus. In this case, the band of the resonance signal becomes $l_h \cdot G_y$ and the limit of sampling frequency is selected as the sampling frequency. In this case, the data number of $l_h \cdot G_y \cdot Y T_2^*/2$ in total can be obtained. When compared with the case of the bust, this is a value reduced to $l_h/l_B$. If the number of sampling points is the same as that of the bust, the remaining sampling points represent the sampling of portions other than the object to be inspected. Even if the sampling frequency is increased to make up for the decrease in such data points, it does not contribute to resolution, as described already. In the case of inspection of the head, therefore, if $G_y' = -G_y \cdot l_B/l_h (G_y' > G_y)$ is applied as the linear gradient magnetic field $G_y'$, its frequency band becomes $G_y \cdot l_B$ and becomes the same value as that of the bust. Accordingly, the effective sampling points do not decrease even if the same sampling frequency is used, so that higher resolution can be accomplished in comparison with the case in which the intensity of the linear gradient magnetic field is not changed.

Figure 4:
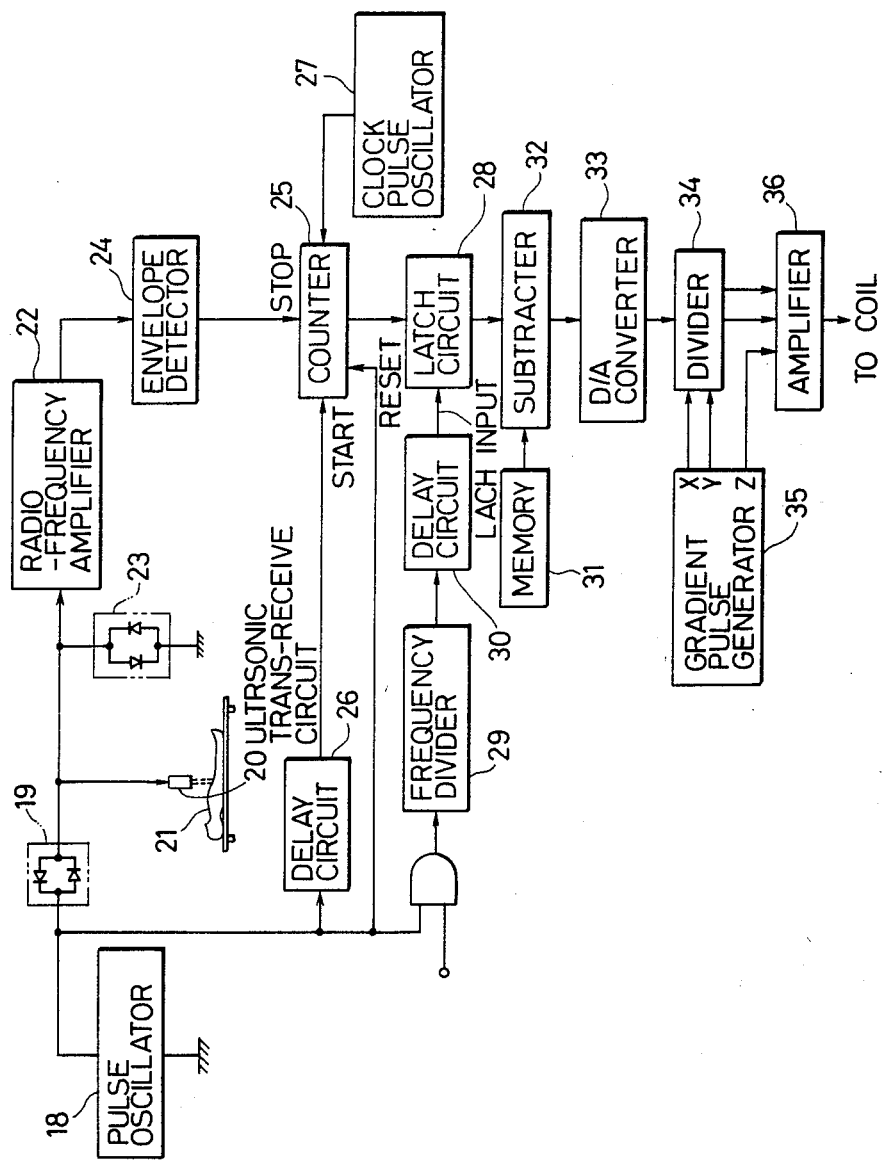
FIGS. 4 and 5 show the principal portions of the imaging apparatus of the present invention, respectively.

FIG. 4 illustrates the principal portions of one embodiment of the present invention and shows the construction of an apparatus in which the size of the object to be inspected is detected by ultrasonic wave and the intensity of the linear gradient magnetic field is changed in accordance with the detection signal. The output from a pulse oscillator 18 passes through a trans-receive separation circuit 19 consisting of two diodes that are juxtaposed with each other in opposite directions, and is then applied to a ultrasonic trans-receive circuit 20, which in turn radiates the ultrasonic wave to the object 21 to be inspected. Resolution of 1 cm can be obtained if a ultrasonic wave of a 300 kHz frequency and 30 μsec pulse length (corresponding to 10 wavelength) is used. The reflected wave from the object 21 to be inspected is received by the same trans-receive circuit 20 and is then amplified by a radio frequency amplifier 22 and the envelope is detected by an envelope detector 24, producing a stop pulse to a counter 25. Reference numeral 23 represents a circuit which prevents the transmission pulse from being impressed to the amplifier 22 and consists of two diodes juxtaposed with each other in opposite directions. The pulse from the pulse oscillator 18 also passes through a delay circuit 26 and is used for producing the start pulse to the counter 25 and for resetting directly the counter 25. The delay circuit 26 is disposed so as to feed the start pulse after the counter 25 is reset by the pulse from the pulse oscillator 18.

The counter 25 counts the clock pulses from the clock pulse generator 27 from the start pulse described above and finishes counting upon receiving the stop pulse. Accordingly, this counter 25 measures the time from the radiation of the ultrasonic pulse from the ultrasonic trans-receive circuit 20 and the return of the pulse after being reflected from the object 21 to be inspected. The time required for the ultrasonic wave to go to the object 21 from the trans-receive circuit 20 and come back therefrom is $\tau = n/f_c$ with $f_c$ and n representing the frequency of the clock pulse and the number of count, respectively. Hence, the distance $l_o$ between the ultrasonic trans-receive circuit 20 and the object 21 to be inspected is given by $$l_o = \tfrac{1}{2}\tau v,$$

where v is the velocity of sound in the air which is 340 m/s at room temperature. The value of the counter 25 is held by a latch circuit 28 until a latch input is applied. The latch input in this case is obtained by dividing the frequency of the pulse from the pulse oscillator 18 by a frequency divider 29 and delaying it by a delay circuit 30. If the repetition frequency of the pulse oscillator may be from a few Hz to 100 Hz and in this case, no pulse overlap occurs from transmission to reception. Accordingly, the distance can be calculated by this frequency and the frequency after frequency division. If data need not be frequently updated, however, the latch input can be kept off by interposing an AND circuit between the pulse oscillator 18 and the frequency divider 29 and changing over the input of this AND circuit.

The data thus obtained are then subtracted by a subtractor 32 between a memory 31 storing a numeric value obtained by dividing the distance between the trans-receive circuit 20 and a bed 51 by $f_c$ and become a value corresponding to the size of the object to be inspected. This value is subjected to D-A conversion by a digital-to-analog (D-A) converter 33 and is applied to a divider 34. Another input, which is from an X-Y direction gradient pulse generator 35, is also applied to the divider 34 and the quotient of these inputs is applied as an input to an amplifier 36 for the gradient field generating coil. Incidentally, the amplifier 36 corresponds to the coil driving devices 6, 7 and 8 shown in FIG. 1. In conjunction with the Z direction, the input is directly applied from 35 to 36. If planes other than the X-Y plane are to be imaged, the same method may naturally be used for the Z direction, too. Incidentally, the trans-receiver circuit 20 for the ultrasonic wave may be fitted to the coil 3 or 4 by boring a hole on the bobbin of the coil so that the ultrasonic wave reaches the object to be inspected. Alternatively, the size of the object to be inspected is in advance measured at a predetermined position before the object is inserted into the coil 3 or 4.

Figure 5:
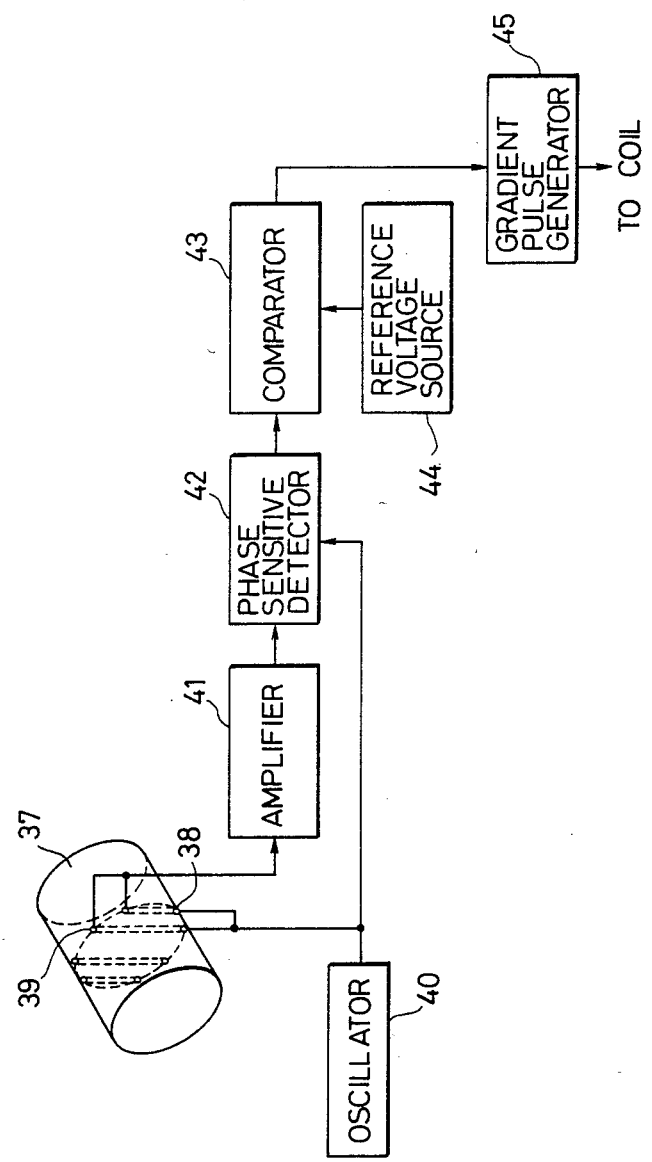

FIG. 5 shows the principal portions of the apparatus in accordance with another embodiment of the present invention. The apparatus detects the size of the object to be inspected by light beams and changes the intensity of the linear gradient magnetic field.

The apparatus of this embodiment determines two kinds of sizes, that is, the head and the bust, that are necessary for the ordinary inspection. The intensity each of the linear gradient magnetic fields for the head and the bust or abdomen is set in advance.

A light emitting diode 38 and a photodiode 39 are disposed in the bobbin 37 of the coil for generating the radio frequency magnetic field or linear gradient magnetic field so as to face each other. The light emitting diode 38 is actuated by an oscillator 40. Since the output of the photodiode 39 changes with the size of the object to be inspected, it is amplified by the amplifier 41 and is then detected synchronously by a phase sensitive detector 42 with a frequency from the oscillator 40 as the reference signal. The frequency band can be arbitrarily narrowed by means of synchronous detection so that the influences of noise light from the circumference can be eliminated. The output of the phase sensitive detector 42 is compared with a voltage from a reference voltage source 44 by a comparator 43 and produces the logic "1" or "0" in accordance with the difference. A gradient pulse generator 45 selects predetermined gradient field intensity in accordance with this value and drives the coil for generating the linear gradient magnetic field.

The intensity value of the linear gradient magnetic field is stored in an RAM or ROM. The value is read out, is amplified by some multiples and is thereafter applied to the gradient pulse generator 45. The output of the comparator 43 is used so as to change the gain of this amplifier. Incidentally, it is necessary that the object to be inspected should be laid down on a bed which permits the passage of light.

Besides the method of automatically detecting the size of the object to be inspected and changing the intensity of the linear gradient magnetic field as in the embodiments described above, the operator of the apparatus by himself can apply a numeric value from a console to the divider 34 shown in FIG. 4 or can apply the value to the gradient pulse generator 45 shown in FIG. 5.

As described in detail in the foregoing, the present invention always provides optimal spatial resolution in the imaging apparatus using nuclear magnetic resonance by changing the intensity of the linear gradient magnetic field in accordance with the size of the object to be inspected or with the size of the inspection zone.

What is claimed is:

1. An imaging apparatus using nuclear magnetic resonance, comprising:
   field generation means for generating a static magnetic field, a linear gradient magnetic field and a radio frequency magnetic field, respectively, and for exciting nuclear spins in an object to be inspected so as to produce a nuclear magnetic resonant signal when said object is located in a magnetic field having a predetermined spatial gradient;
   signal detection means for detecting the nuclear magnetic resonant signal which is indicative of a projection of a nuclear spin distribution in said object to be inspected;
   a computer responsive to said signal detection means for calculating an imaging signal;
   output means for displaying the imaging signal from said computer; and
   control signal generation means for generating a control signal for controlling the intensity of said linear gradient magnetic field, said control signal having a value indicative of the size of said object to be inspected;
   said linear gradient magnetic field generation means being responsive to said control signal generation means for providing said predetermined spatial gradient corresponding to said control signal.

2. The imaging apparatus using nuclear magnetic resonance as defined in claim 1, wherein said control signal generation means comprise detection means for detecting a value indicative of the size of said object to be inspected and means for generating said control signal indicative of the detected size of said object to be inspected.

3. The imaging apparatus using nuclear magnetic resonance as defined in claim 2, wherein said detection means for detecting a value indicative of the size of said object to be inspected comprise means for transmitting ultrasonic wave to said object to be inspected, means for receiving the ultrasonic wave from said object to be inspected and means for generating an electric signal indicative of the time required for transmission and reception of said ultrasonic wave as an indication of the size of said object.

4. The imaging apparatus using nuclear magnetic resonance as defined in claim 3, wherein said means for generating the electric signal comprises a generator for generating clock pulse signals and a counter connected to said generator and responsive to said transmitting means and receiving means for counting the clock pulse signals from the transmission to reception of the ultrasonic wave and producing an output indicative of the number of clock pulse signals counted.

5. The imaging apparatus using nuclear magnetic resonance as defined in claim 3 or 4, wherein said linear gradient magnetic field generation means comprise a coil for generating the linear gradient magnetic field, current generation means for feeding a current to said coil and control means for controlling the feed current in accordance with the control signal from said control signal generating means.

6. The imaging apparatus using nuclear magnetic resonance as defined in claim 2, wherein said means for detecting a value indicative of the size of said object to be inspected comprise means for radiating a luminous flux, light detection means for receiving said luminous flux and means for generating an electric signal corresponding to the quantity of said luminous flux received by said light detection means.

7. The imaging apparatus using nuclear magnetic resonance as defined in claim 6, wherein said means for generating the electric signal includes detection means for synchronously detecting the output signal of said light detection means with a reference signal representing an output signal of an oscillator used for driving said means for radiating said luminous flux.

8. The imaging apparatus using nuclear magnetic resonance as defined in claim 6, wherein said means for generating the control signal include comparison means for comparing an electric signal corresponding to the light quantity of said received luminous flux with a predetermined reference value and generating a signal indicative of the difference therebetween.

9. The imaging apparatus using nuclear magnetic resonance as defined in claim 7 or 8, wherein said linear gradient magnetic field generation means comprise a coil for generating a linear gradient magnetic field, current generation means for feeding a current of a predetermined value to said coil and means for changing the gain of said current generation means in correspondence with the control signal from the control signal generating means.

10. The imaging apparatus using nuclear magnetic resonance as defined in claim 1, wherein said control signal generation means generates a control signal having a value so that the intensity of said linear gradient magnetic field is inversely proportional to the size of said object to be inspected.

11. An imaging apparatus using nuclear magnetic resonance comprising:
    static field generation means for generating a static magnetic field:
    exciting means for exciting nuclear spins of an object to be inspected, the object being located within said static magnetic field by applying a radio frequency magnetic field to the object;
    signal detection means for periodically detecting a nuclear magnetic resonant signal produced by the excitation of the nuclear spins:
    gradient field generation means for generating a linear gradient magnetic field for application to the object, the gradient magnetic field intensity of the gradient magnetic field being set to a predetermined value at least within a period of detection of the nuclear magnetic resonant signal by the signal detection means so that the nuclear magnetic resonant frequency of the object has a spatial gradient, the nuclear magnetic resonant signal being indicative of a projection of nuclear spin distribution in the object;

computer means responsive to the signal detection means for transforming a detected signal therefrom into an imaging signal;

output means for displaying an image in response to the imaging signal from the computer means; and control means for generating a control signal for determining the predetermined value of the gradient magnetic field intensity, the predetermined value being determined so as to be inversely proportional with one of the size of the object to be inspected and a size of an inspection zone, the gradient field generation means being responsive to the control signal generated by the control means for generating the linear gradient magnetic field intensity of the predetermined value corresponding to the control signal.

12. The imaging apparatus as defined in claim 11, wherein the control means includes detection means for detecting a value indicative of the size of the object to be inspected and for providing a signal indicative thereof, and means responsive to the output signal indicative of the size detecting means for producing the control signal for setting the predetermined value of the linear gradient magnetic field intensity in correspondence therewith.

13. The imaging apparatus as defined in claim 12, wherein the size detection means includes means for transmitting an ultrasonic wave to the object to be inspected and receiving a reflected ultrasonic wave and for providing an output signal indicative of the time required for transmission and reception as an indication of the size of the object.

14. The imaging apparatus as defined in claim 13, wherein the linear gradient magnetic field operation means includes a coil for generating the linear gradient magnetic field, current generation means for feeding a current to the coil, and current control means for controlling the feed current in accordance with the control signal from the control signal generating means so as to set the gradient magnetic field intensity to the predetermined value.

15. The imaging apparatus as defined in claim 12, wherein the means for detecting a value indicative of the size of the object to be inspected includes means for radiating a luminous flux, light detection means for receiving the luminous flux, and means responsive to the light detection means for generating an output signal corresponding to the quantity of the luminous flux received as an indication of the size of the object.

16. The imaging apparatus as defined in claim 15, wherein the control means for generating a control signal includes comparison means for comparing the output signal corresponding to the quantity of the received luminous flux with a reference value and providing an output signal indicative of the difference therebetween.

17. The imaging apparatus as defined in claim 15 or 16, wherein the gradient field generation means includes a coil for generating a linear gradient magnetic field, current generation means for feeding a current of a first value to the coil, and means responsive to the control signal from the control means for changing the gain of the current generation means in correspondence with the control signal so that the gradient magnetic field intensity is set to the predetermined value.

* * * * *